US00PP09828P

United States Patent [19]

Spira et al.

[11] Patent Number: Plant 9,828

[45] Date of Patent: Mar. 18, 1997

[54] ASIAN PEAR TREE NAMED "ASIO 3"

[75] Inventors: Joel S. Spira; Ruth R. Spira, both of Coopersburg; Eugene S. Konno, Germansville; Neil J. Vincent, Quakertown, all of Pa.

[73] Assignee: Subarashii Kudamono Co., Inc., Coopersburg, Pa.

[21] Appl. No.: 531,184

[22] Filed: Sep. 19, 1995

[51] Int. Cl.[6] ..... A01H 5/00

[52] U.S. Cl. ..... Plt./36

[58] Field of Search ..... Plt./36

*Primary Examiner*—James R. Feyrer

*Attorney, Agent, or Firm*—Burns, Doane, Swecker & Mathis

[57] ABSTRACT

A new and distinct variety of Asian Pear, botanically known as *Pyrus pyrifolia* is provided. The new cultivar forms attractive extra large substantially round fruit having a dark brown russet surface with tan lenticels and a distinctive semi-sweet mild flavor. The tree and exhibits moderate vigor and possesses a well-branched and an open spreading growth habit. The leaves are medium green in coloration with pinnate moderately-branched venation and a cuspidate apex. Picking of the fruit commonly can begin during late September at Coopersburg, Pa., U.S.A. Substantial and consistent fruit crops are formed.

3 Drawing Sheets

SUMMARY OF THE INVENTION

The present invention comprises a new and distinct cultivar of Asian Pear, botanically known as *Pyrus pyrifolia*, and hereinafter is referred to by the cultivar name 'Asio 3'.

The new cultivar germinated from a seed as a distinctive seeding during the summer of 1983 while growing in a test orchard at 1506 Pleasant View Road, Coopersburg, Pa., U.S.A. The new cultivar was discovered among many open-pollinated seedlings of an Asian Pear tree designated No. 6 (non-patented in the United States) that were planted for test purposes. The seed that produced the No. 6 parent was obtained from Japan and was formed on open-pollinated Asian Pear trees. It is impossible to further identify the origin of the No. 6 parent. The seed that produced the new cultivar of the present invention was formed at Coopersburg, Pa., U.S.A. The male parent of the new cultivar is unknown. A large number of Asian Pear varieties were growing in the area as well as a few varieties of European Pear. It is impossible to identify the parent plants of the new cultivar. A single tree of the new cultivar was discovered in the test orchard following selective study and initially was designated No. 530.

Since 1987 the original tree of the new cultivar has annually produced a crop of high quality Asian Pears.

It was found that the new 'Asio 3' cultivar of the present invention:

(a) forms attractive late mid-season extra large substantially round fruit having a dark brown russet surface with tan lenticels and a semi-sweet mild flavor, (b) forms a medium-sized tree having a well-branched and an open spreading growth habit, and (c) forms generally ovate medium green leaves with pinnate venation and a cuspidate apex.

It was found that the new 'Asio 3' cultivar forms fruit that is substantially round unlike the more conical fruit of the No. 6 parent. Also, the fruit of the 'Asio 3' cultivar exhibits a distinctive mild semi-sweet flavor unlike the more tart flavor of the No. 6 parent.

When the 'Asio 3' cultivar is compared to the 'Olympic' cultivar (non-patented in the United States), it is found that each forms extra large fruit of substantially the same configuration. However, the 'Asio 3' cultivar exhibits fruit having a darker brown skin coloration, a milder flavor, and a flesh texture that is slightly less crisp when mature.

Asexual reproduction of the new cultivar by budding on 'Bartlett' rootstock carried out at aspers, Pa., U.S.A. beginning during 1987, has demonstrated that the characteristics of the new cultivar as herein disclosed are firmly fixed and are retained through successive generations of such asexual propagation.

'Asio 3' has not been observed under all possible environmental conditions to date. Accordingly, it is possible that the phenotype may vary somewhat with variations in the environment, such as temperature, light, day length, contact with pesticides, etc.

BRIEF DESCRIPTION OF THE PHOTOGRAPHS

The accompanying photographs show in color as nearly true as it is reasonably possible to make the same in color illustrations of this character the original tree of the new variety as well as plant parts thereof. The spreading tree was approximately 11 years of age and was growing on its own roots at 1506 Pleasant View Road, Coopersburg, Pa., U.S.A. All photographs with the exception of FIG. 6 were taken on Sep. 14, 1994.

DETAILED DESCRIPTION

Figure 1:
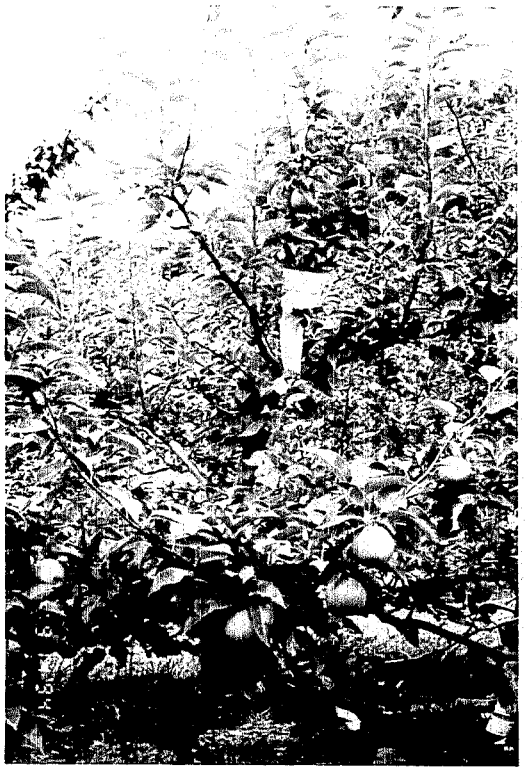
FIG. 1 illustrates the entire tree of the new variety wherein the medium tree size and the well-branched, spreading, and open growth habit are apparent.

The chart used in the identification of the colors described hereafter is The R.H.S. Colour Chart of The Royal Horticultural Society, London, England. In some instances common color terms are used which are to be accorded their ordinary dictionary significance. The trees described were being grown under standard orchard conditions at Coopersburg, Pa., U.S.A.

Classification:

*Botanical.*—*Pyrus pyrifolia* (*P. serotina*), cv. 'Asio 3'.

*Commercial.*—Asian Pear.

Tree:

*Size.*—Medium. The original tree at the age of 12 years is approximately 13 feet tall. Three years following the field planting of a tree that was budded 1½ years earlier on 'Bartlett' rootstock, a tree height of approximately 5 feet commonly will be observed. Five years following field planting of a tree that was budded 1½ years earlier on 'Bartlett' rootstock, a tree height of approximately 8 feet commonly will be observed.

*Growth habit.*—Moderate vigor.

*Configuration.*—Spreading.

*Density.*—Open and well-branched.

*Hardiness.*—Hardy in wood and bud.

*Fruit bearing.*—Productive.

*Bearing habit.*—Annually on second-year and older wood with the fruit being borne laterally and terminally on second year and older shoots, as well as laterally on spurs.

*Trunk.*—Medium diameter and deeply grooved.

*Branches.*—Thickness: medium, strong, and tend to be flattened on one side. Bark texture: smooth (as illustrated). Frequency: moderate branching density with approximately 4 to 6 branches typically originating per two feet of trunk. However, the leaf mass per unit of tree volume commonly is less than that of a typical Asian Pear tree thereby resulting in a somewhat reduced canopy density. Branch angles: the angles of the main scaffold branches commonly are approximately 45 degrees under natural growing conditions. Such branches typically settle to approximately 60 to 90 degrees under the weight of the fruit load. When limb spreaders are employed, branch angles of approximately 90 degrees can be achieved thereby resulting in earlier fruit bearing. Bark color: medium brown on younger wood. Lenticels: some prominent and tan in coloration.

Figure 2:
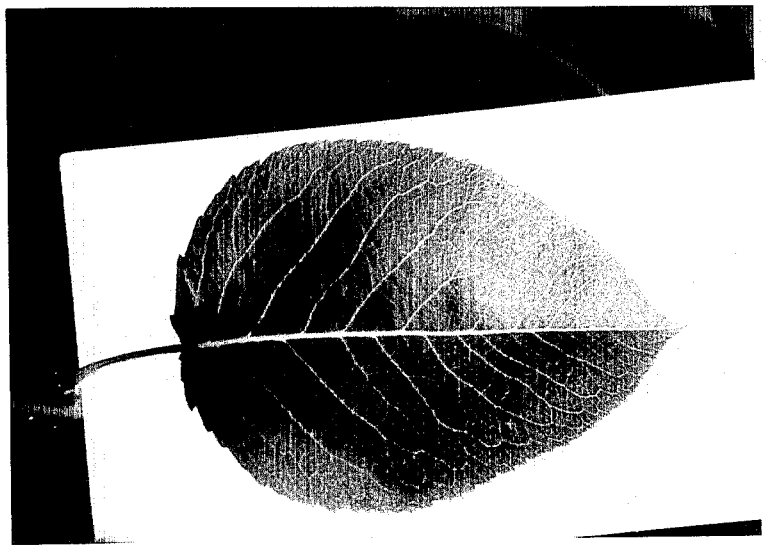
FIG. 2 illustrates a typical generally ovate leaflet of the new variety wherein the serration pattern, moderate pinnate venation, and cuspidate apex are more readily apparent.
Figure 3:
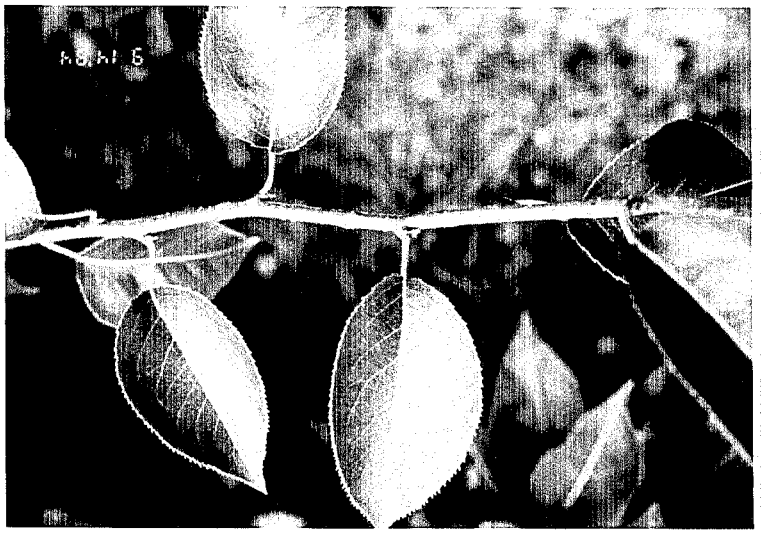
FIG. 3 illustrates a typical limb of the new variety wherein the generally ovate leaves with finely serrated edges are apparent.
Figure 4:
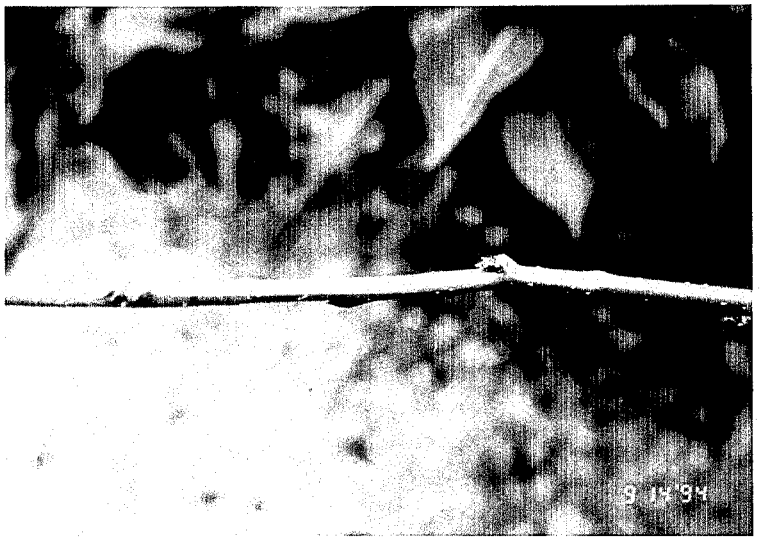
FIG. 4 illustrates a typical limb of the new variety wherein the leaves have been removed so that the smooth appearance of the limb is unobstructed.
Figure 5:
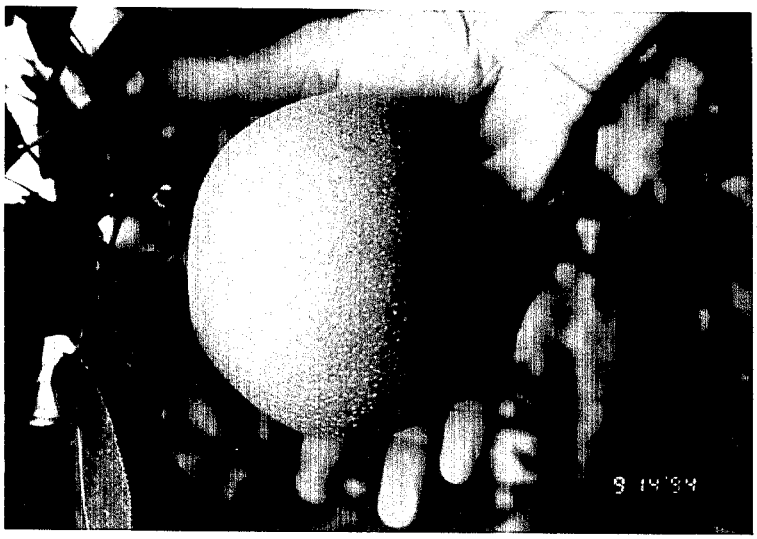
FIG. 5 illustrates a specimen of an extra large dark brown russet fruit of the new variety shortly prior to full maturity while present on the tree.
Figure 6:
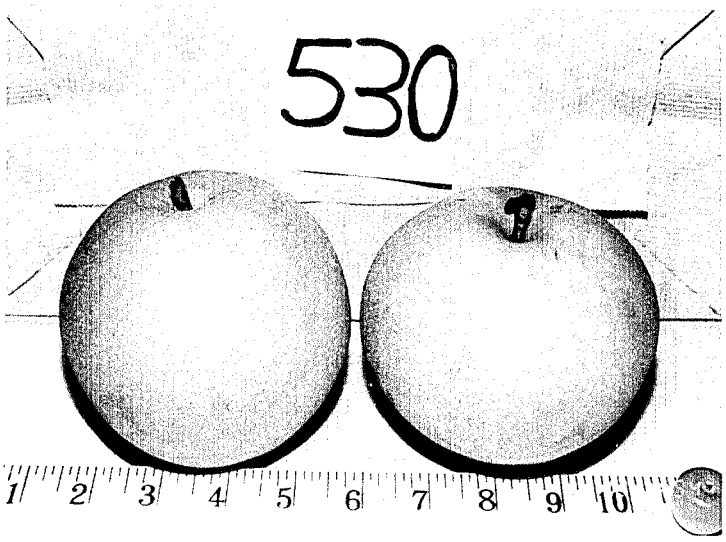
FIG. 6 illustrates additional specimens of the fruit of the new variety that was harvested during late September, 1994, placed in refrigerated storage at approximately 32° F., and removed from such storage and photographed on Dec. 4, 1994. A measuring stick in inches is provided at the bottom of the photograph for comparative purposes.

*Leaves.*—Size: long, commonly approximately 11.3 cm. in length on average. Configuration: generally ovate. Base: rounded. Apex: cuspidate. Margin: serrulate (as illustratd in FIG. 2). Venation: pinnate with many fine branches. Thickness: medium. Color upper surface: during a typical growing season is medium green, Green Group 135A, and during the fall is Yellow-Green Group 21A. Color under surface: during a typical growing season is silvery green, Yellow-Green Group 138A, and during the fall is Orange Group 26B. Petiole: medium in length, and commonly approximately 3.5 cm. in length.

*Flowers.*—Season: mid-season, and generally concurrent with the 'Olympic' cultivar. During 1993, the first bud break occurred on April 16th, and full bloom occurred on May 1st. During 1994, the first bud break occurred on April 16th, and full bloom occurred on April 26th. Size: medium, and commonly approximately 3.3 cm in diameter on average. Color: white, White Group 155A. Pollen: viable pollen is produced which has enabled 'Asio 3' to be utilized as a pollen parent in interspecific crosses that have been carried out annually since 1988. When attempts have been made to self-pollinate 'Asio 3', no resulting fruit has set to date. Accordingly, the preliminary indications are that 'Asio 3' may be self-infertile. bearing: commonly in a corymb of 6 to 8 flowers. Configuration: the reproductive organs are typical of the species. The flowers generally possess five pistils and bear fruit having five sets of carpels. However, some flowers have been observed having six pistils. When six pistils are present, one pistil commonly is substantially shorter than the others, but is viable as evidenced by the recovery of fruit specimens bearing approximately 11 to 12 seeds.

*Fruit.*—Season of maturity: late mid-season maturing approximately the same as the 'Olympic' cultivar. During 1993, the first picking was on September 25th and the last picking was on October 10th. During 1994, the first picking was on September 27th and the last picking was on October 7th. Bearing: most of the fruit is borne laterally on spurs; however, some fruit also can be produced laterally on shoots. Size: extra large, and commonly approximately 9 to 12 cm. in diameter. The fruit weight commonly ranges from approximately 350 to 600 grams. It is recommended that the fruit be thinned in order to encourage the formation of the larger-sized fruit within the specified range. If the fruit is unthinned the tree will nevertheless produce fruit of marketable size; however, tree damage may occur due to the weight of the fruit. Configuration: substantially round. Neck: absent. Stem: medium in length, thick, and clubbed. Cavity: acuminate. Basin: obtuse. Calyx: open, and deciduous. Skin: green ground cover with dark brown russet surface and numerous lighter tan lenticels (as illustrated). The lenticels sometimes are prominent. The skin is completely russet. The skin commonly is Greyed-Orange Group 164A, and the lenticels commonly are Greyed-Orange Group 165D. Flesh: very juicy, white, and crisp. The degree of crispness at maturity is slightly less than that of the 'Olympic' cultivar. Flavor: semi-sweet (TSS 10 to 12 Brix), and mild with low acid. The distinctive fruit flavor of the new cultivar is milder than that of the 'Olympic' cultivar. The fruit flavor is very mild. The sweetness of the fruit is believed to be much less intense than that of the 'Olympic' cultivar. Such fruit flavor is believed to be substantially uniform throughout the fruit. Core: median. Carpels: elliptical, with axial symmetry. Seeds: commonly 6 to 10 per fruit, commonly 1 or 2 per carpel, medium-sized, commonly flattened on one side, and dark brown in coloration. Quality: very good. Keeping quality: very good, can be stored at least 2 months in good condition at 32° F. Fire blight resistance: no inoculations for fire blight screening have been carried out; however, it is believed that at least some resistance to fire blight is being exhibited. For instance, when fire blight strikes have occured in the orchard where 'Asio 3' was being grown, no fire blight has been observed in 'Asio 3'.

We claim:

1. A new and distinct cultivar of Asian Pear, substantially as illustrated and described, which:

(a) forms attractive late mid-season extra large substantially round fruit having a dark brown russet surface with tan lenticels and a semi-sweet mild flavor, (b) forms a medium-sized tree having a well-branched and an open spreading growth habit, and (c) forms generally ovate medium green leaves with pinnate venation and a cuspidate apex.

* * * * *